(12) United States Patent
Lovell et al.

(10) Patent No.: US 9,835,621 B2
(45) Date of Patent: Dec. 5, 2017

(54) PROCESS FOR DETECTION OF ALZHEIMER'S DISEASE FROM A SERUM SAMPLE

(75) Inventors: Mark A. Lovell, Mt Vernon, KY (US); Bert C. Lynn, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/232,863

(22) PCT Filed: Jul. 16, 2012

(86) PCT No.: PCT/US2012/046925
§ 371 (c)(1),
(2), (4) Date: Jun. 26, 2014

(87) PCT Pub. No.: WO2013/010170
PCT Pub. Date: Jan. 17, 2013

(65) Prior Publication Data
US 2014/0302535 A1    Oct. 9, 2014

Related U.S. Application Data

(60) Provisional application No. 61/572,329, filed on Jul. 14, 2011, provisional application No. 61/566,971, filed on Dec. 5, 2011.

(51) Int. Cl.
| | | |
|---|---|---|
| *G01N 33/53* | (2006.01) | |
| *G01N 33/566* | (2006.01) | |
| *G01N 33/567* | (2006.01) | |
| *G01N 33/543* | (2006.01) | |
| *G01N 33/68* | (2006.01) | |

(52) U.S. Cl.
CPC ... *G01N 33/54306* (2013.01); *G01N 33/6896* (2013.01); *G01N 2333/76* (2013.01); *G01N 2333/99* (2013.01); *G01N 2800/2821* (2013.01)

(58) Field of Classification Search
None
See application file for complete search history.

(56) References Cited

U.S. PATENT DOCUMENTS

2005/0244890 A1    11/2005    Davies et al.
2008/0026405 A1    1/2008     Lovell et al.

OTHER PUBLICATIONS

Lovell M.A. et al.: An aberrant protein complex in CSF as a biomarker of Alzheimer disease, Neurology, vol. 70. No. 23. Jun. 3, 2008, p. 2212-8.
Du J. et al.: Characterization of the interaction of beta-amyloid with transthyretin monomers and tetramers, Biochemistry, vol. 49. No. 38, Sep. 28, 2010 (Sep. 28, 2010). pp. 8276-8289.
Reiber H.: Dynamics of brain-derived proteins in cerebrospinal fluid, Clin. Chim. Acta, vol. 310. No. 2., Aug. 20, 2001.(Aug. 20, 2001). pp. 173-186.
Davidson, et al., Proteome studies of CSF in AD patients. Mech Ageing Dev, 2006. 127(2): p. 133-7.
Serot, et al., Cerebrospinal fluid transthyretin: aging and late onset Alzheimer's disease. J Neurol Neurosurg Psychiatry, 1997. 63(4): p. 506-8.

*Primary Examiner* — Olga N Chernyshev
(74) *Attorney, Agent, or Firm* — Stites & Harbison PLLC; Mandy Wilson Decker; Rachel Rutledge

(57) ABSTRACT

Disclosed is a method of detecting a concentration of a biomarker in a human subject having or being at risk of developing Alzheimer's disease or Mild Cognitive Impairment (MCI). Also disclosed is a process for detecting a concentration of a biomarker in a human subject having or being at risk of developing Alzheimer's disease or Mild Cognitive Impairment (MCI) comprising (a) detecting a first concentration of lipocalin-PDS/TTR complex in a blood sample or urine sample from the subject, (b) determining a second concentration of PDS/TTR complex in a blood sample or urine sample from an unaffected individual, and (c) comparing the first and second concentrations, wherein a lower first concentration as compared to the second concentration is indicative of the subject having or being at risk of developing Alzheimer's disease.

11 Claims, 1 Drawing Sheet

PROCESS FOR DETECTION OF ALZHEIMER'S DISEASE FROM A SERUM SAMPLE

RELATED APPLICATION

This application claims priority under 35 U.S.C. 119(e) to provisional application U.S. Ser. No. 61/572,329, filed Jul. 14, 2011 and to provisional application U.S. Ser. No. 61/566,971, filed Dec. 5, 2011, which applications are incorporated hereby by reference.

FIELD OF THE INVENTION

The present invention relates to the field of detection and monitoring of neurodegenerative disorders, including Alzheimer's disease (AD) and mild cognitive impairment (MCI). More particularly, the present invention relates to proteinaceous biomarkers that can be measured in biological fluids, which can be used to aid in the detection of neurodegenerative disorders, including Alzheimer's disease and mild cognitive impairment.

BACKGROUND OF THE INVENTION

Previous studies suggest there is diminished transport capacity of high molecular weight (>30 kDa) material through choroid plexus epithelial cells in the progression of AD. Further, it has been observed that $A\beta_{1-42}$ levels are significantly lower in serum compared to CSF because of deposition in senile plaques (Solfrizzi, V, D'Introno, A, Colacicco, A M, Capurso, C, Todarello, O, et al. Circulating biomarkers of cognitive decline and dementia *Clin Chim Acta*, 2006; 364:91-112). There is an ongoing need for methods for detecting biomarkers associated with AS and MCI.

SUMMARY OF THE INVENTION

In certain embodiments, the present invention provides method of detecting a concentration of a biomarker in a human subject having or being at risk of developing Alzheimer's disease (AD) or Mild Cognitive Impairment (MCI), the method comprising: (a) detecting a first concentration of lipocalin-PDS/TTR complex in a blood sample or urine sample from the subject, (b) determining a second concentration of PDS/TTR complex in a blood sample or urine sample from an unaffected individual, and (c) comparing the first and second concentrations, wherein a lower first concentration as compared to the second concentration is indicative of the subject having or being at risk of developing AD or MCI.

In certain embodiments, the present invention provides a method of detecting a concentration of a biomarker in a human subject having or being at risk of developing Alzheimer's disease (AD) or Mild Cognitive Impairment (MCI), the method comprising: (a) detecting a concentration of lipocalin-PDS/TTR complex in a blood sample or urine sample from the subject, (b) comparing the concentration to a reference value, wherein a lower concentration as compared to the reference value is indicative of the subject having or being at risk of developing Alzheimer's disease or MCI.

In certain embodiments, the present invention provides a kit comprising: (a) a solid substrate; (b) a trapping binding ligand specific for lipocalin-PDS bound to the solid substrate; (c) a probing binding ligand specific for TTR; (d) optionally, instructions for using the kit to detect PDS/TTR in a blood sample or urine sample.

In certain embodiments, the present invention provides a method of isolating a lipocalin-PDS/TTR complex biomarker from blood or urine comprising: (a) contacting the blood or urine with a trapping binding ligand specific for lipocalin-PDS to form a trapped biomarker, wherein the trapping binding ligand specific for lipocalin-PDS is bound to a solid substrate; (b) contacting the trapped biomarker with a probing binding ligand that is specific for TTR to form a probed biomarker complex; and (c) purifying the probed biomarker complex.

In certain embodiments, the present invention provides a process for detecting Alzheimer's disease in a human subject, the process comprising obtaining a sample of blood from the subject, optionally preparing a sample of serum or plasma from the sample of blood, determining the concentration of PDS/TTR in the sample of blood, and comparing the concentration of PDS/TTR to a reference value.

DETAILED DESCRIPTION

Figure 1:
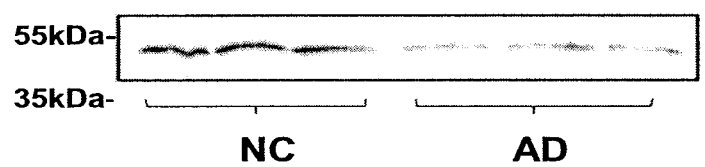
FIG. 1. The PDS/TTR complex was immunoprecipitated from representative serum specimens from normal control (NC) and probable AD (AD) subjects using rabbit anti-TTR and was visualized using mouse anti-PDS. There was a significant decrease of immunostaining for the PDS/TTR complex in serum from AD patients (34.8±2.5% control) compared to NC subjects (100±2.9%).

Surprisingly, the inventors found that levels of the lipocalin-PDS/TTR complex biomarker in a blood sample were lower in subjects with Alzheimer's disease than in non-diseased controls. The art had taught away from this finding, in that, according to the art, levels of the biomarker in cerebrospinal fluid were higher in subjects with Alzheimer's Disease than in non-diseased controls.

Surprisingly, the inventors found that levels of the biomarker in a blood sample were lower in subjects with Mild Cognitive Impairment than in non-diseased controls. The art had taught away from this finding, in that, according to the art levels of the biomarker in cerebrospinal fluid were higher in subjects with Mild Cognitive Impairment than in non-diseased controls.

In certain embodiments, the present invention provides a concentration of a biomarker in a human subject having or being at risk of developing Alzheimer's disease (AD) or Mild Cognitive Impairment (MCI), the method comprising: (a) detecting a first concentration of lipocalin-PDS/TTR complex in a blood sample or urine sample from the subject, (b) determining a second concentration of PDS/TTR complex in a blood sample or urine sample from an unaffected individual, and (c) comparing the first and second concentrations, wherein a lower first concentration as compared to the second concentration is indicative of the subject having or being at risk of developing AD or MCI. In certain embodiments, the blood sample is a sample of whole blood, serum, plasma, or a subcomponent of blood. In certain embodiments, the blood sample is a serum or plasma sample. As used herein, the term "blood sample" includes a whole blood sample or a subcomponent sample (e.g., a serum sample). In certain embodiments, the lipocalin-PDS/TTR complex is a trimer consisting of one molecule of lipocalin-PDS and two molecules of TTR. In certain embodiments, the lipocalin-PDS/TTR complex binds to a trapping binding ligand specific for lipocalin-PDS but not to a binding ligand specific for hematopoietic-PDS/TTR complex. In certain embodiments, the binding ligand is an antibody. In certain embodiments, the lipocalin-PDS/TTR complex is a modified lipocalin-PDS/TTR complex that further comprises alpha and/or beta-unsaturated aldehydic by-products of lipid peroxidation. In certain embodiments, the lipocalin-PDS/TTR complex binds to a probing binding ligand specific for TTR. In certain embodiments, the probing ligand specific for TTR further comprises a label generating a detectable signal. In certain embodiments, the label comprises a chemical, an enzymatic, a radioactive, a fluorescent, a luminescent, a chemiluminescent and a FRET label. In certain embodiments, the detection of the first concentration of lipocalin-PDS/TTR complex is by ELISA.

In certain embodiments, the present invention provides a method of detecting a concentration of a biomarker in a human subject having or being at risk of developing Alzheimer's disease (AD) or Mild Cognitive Impairment (MCI), the method comprising: (a) detecting a concentration of lipocalin-PDS/TTR complex in a blood sample or urine sample from the subject, (b) comparing the concentration to a reference value, wherein a lower concentration as compared to the reference value is indicative of the subject having or being at risk of developing Alzheimer's disease or MCI.

In certain embodiments, the present invention provides a kit comprising: (a) a solid substrate; (b) a trapping binding ligand specific for lipocalin-PDS bound to the solid substrate; (c) a probing binding ligand specific for TTR; (d) optionally, instructions for using the kit to detect PDS/TTR in a blood sample or urine sample. In certain embodiments, the solid substrate is a hydrocarbon polymer, glass, metal, or gel. In certain embodiments, the solid substrate is a gelatin, latex, polystyrene, colloidal gold, or magnetic bead. In certain embodiments, trapping binding ligand specific for lipocalin-PDS but not to a binding ligand specific for hematopoietic-PDS.

In certain embodiments, the present invention provides a method of isolating a lipocalin-PDS/TTR complex biomarker from blood or urine comprising: (a) contacting the blood or urine with a trapping binding ligand specific for lipocalin-PDS to form a trapped biomarker, wherein the trapping binding ligand specific for lipocalin-PDS is bound to a solid substrate; (b) contacting the trapped biomarker with a probing binding ligand that is specific for TTR to form a probed biomarker complex; and (c) purifying the probed biomarker complex. In certain embodiments, the present invention provides a probed biomarker complex isolated according to the method described above.

In certain embodiments, the present invention provides a process for detecting Alzheimer's disease in a human subject, the process comprising obtaining a sample of blood from the subject, preparing a sample of serum from the sample of blood, determining the concentration of PDS/TTR in the sample of serum, and comparing the concentration of PDS/TTR to a reference value. In certain embodiments, Alzheimer's disease is detected if the concentration of PDS/TTR is less than the reference value. In certain embodiments, the sample of blood is collected from the subject by phlebotomy. In certain embodiments, the sample of serum is prepared from the sample of blood by permitting the sample of blood to clot and centrifuging the sample of blood. In certain embodiments, the ELISA is an ELISA described in U.S. Pat. No. 7,851,172. In certain embodiments, the ELISA provides an electromagnetic signal capable of being detected by an optical reader. In certain embodiments, the ELISA provides an electrochemical signal capable of being detected by an electrochemical signal detection apparatus.

A "subject" of analysis, diagnosis, or treatment is an animal. Such animals include mammals, such as a human.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

Detectable Markers and Labels

According to one embodiment, the probing binding ligand has a label generating a detectable signal. The label includes, but not limited to, a chemical (e.g., biotin), an enzymatic (e.g., alkaline phosphatase, peroxidase, β-galactosidase and β-glucosidase, horseradish peroxidase), a radioactive (e.g., $I^{125}$ and $C^{14}$), a fluorescent (e.g., fluorescein), a luminescent, a chemiluminescent or a FRET (fluorescence resonance energy transfer) label. Various labels and methods for labeling binding ligands are well known in the art (Harlow and Lane, eds., Antibodies: A Laboratory Manual (1988) Cold Spring Harbor Laboratory Press, Cold Spring Harbor, N.Y.). In certain embodiments, the probing binding ligand is an antibody that is labeled with biotin or horseradish peroxidase.

As used herein, a "detectable marker" is an atom or a molecule that permits the specific detection of a compound comprising the marker in the presence of similar compounds without a marker. Detectable markers include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The detectable labels used in the assays of the present invention to diagnose Alzheimer's Disease, these labels are attached to the binding agent that is specific for PDS or TTR, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939, 350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrahodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the PDS/TTR complexes are contemplated to be detected in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody that recognizes PDS/TTR complexes in which the antibody is linked to an enzyme (typically by recombinant or covalent chemical bonding). The antibody is detected when the enzyme reacts with its substrate, producing a detectable product. In certain embodiments, enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl)spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4ClN), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

The detection of the lipocalin-PDS/TTR complex can be carried out by various processes well known in the art. This detection can be carried out quantitatively or qualitatively according to conventional procedures, e.g., using various detectable label/substrate pairs as described in Enzyme Immunoassay, E. T. Maggio, ed., CRC Press, Boca Raton, Fla., 1980 and Harlow and Lane, eds. Antibodies: A Laboratory Manual (1988) Cold Spring Harbor Laboratory Press, Cold Spring Harbor, N.Y.

Where the probing binding ligand (e.g., antibody) is labeled with alkaline phosphatase, bromochloroindolylphosphate (BCIP), nitro blue tetrazolium (NBT) and ECF may be used as a substrate for color developing reactions; in the case of labeled with horseradish peroxidase, chloronaphtol, aminoethylcarbazol, diaminobenzidine, D-luciferin, lucigenin (bis-I\Mnethylacridinium nitrate), resorufin benzyl ether, luminol, Amplex Red reagent (10-acetyl-3,7-dihydroxyphenoxazine, TMB (3,3,5,5-tetramethylbenzidine) and ABTS (2,2-Azine-di[3-ethylbenzthiazoline sulfonate]) may be used as a substrate. Other label/substrate pairs include biotin/streptavidin and luciferase/luciferin.

Binding Ligands

The present method uses two types of binding ligands, i.e., a "trapping" (or "capturing") binding ligand and a "probing" (or "detecting") binding ligand. As used herein, the term "trapping binding ligand" means a binding ligand capable of binding to the lipocalin-PDS/TTR complex of interest in biosamples. The term "probing binding ligand" means a binding ligand capable of binding to the lipocalin-PDS/TTR complex captured by the trapping binding ligand. In one embodiment, the binding ligand is an antibody. By "antibody" is meant an immunoglobulin protein which is capable of binding an antigen. Antibody as used herein is meant to include the entire antibody as well as any antibody fragments (e.g., F(ab')$_2$, Fab', Fab, Fv) capable of binding the epitope, antigen or antigenic fragment of interest. As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary. Methods of producing monoclonal, polyclonal and mutant antibodies can be found in US Patent Publication No. 2011-0135689 A1, which is incorporated by reference herein.

As used herein, the term "antibody" includes scFv, humanized, fully human or chimeric antibodies, single-chain antibodies, diabodies, and antigen-binding fragments of antibodies (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv), humanized, fully human or chimeric antibodies, single-chain antibodies, diabodies, and antigen-binding fragments of antibodies (e.g., Fab fragments). A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycine. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

Solid Substrates

According to one embodiment, the trapping binding ligand is bound to a solid substrate. Known materials of this type include hydrocarbon polymers such as polystyrene and polypropylene, glass, metals, and gels. The solid substrate may be in the form of a dipstick, a microtiter plate, a particle (e.g., bead), an affinity column and an immunoblot membrane (e.g., polyvinylidene fluoride membrane) (see U.S. Pat. Nos. 5,143,825; 5,374,530; 4,908,305 and 5,498,551). In certain embodiments, the solid substrate is a microtiter plate.

According to one embodiment, the solid substrate bound to trapping ligands is a bead such as gelatin, latex, polystyrene, colloidal gold or a magnetic bead. The size of these beads may be in the range of 0.3 nm to 20 μm in diameter, and an optimal size can be selected according to the evaluation method to be used. For example, for macroscopic evaluation, it is desirable to employ carriers of 0.2 to 3 μm in diameter with which macroscopic judgment is easier.

Detection Methods and Assays

The present invention provides methods for detecting a complex comprising PDS/TTR in a sample or in vivo. In certain embodiments, Western blots may be used to determine the presence and/or quantity of PDS/TTR in the sample. In certain embodiments or a competitive assay (for example, radioimmunoassay) may be used to determine the presence and/or quantity of PDS/TTR in the sample. For example, one can contact a sample with a binding ligand that is specific for PDS and subsequently contact the bound sample with a binding ligand that is specific for TTR, and detecting the presence or the quantity of bound PDS/TTR. In certain embodiments, the PDS/TTR is detected by means of nuclear magnetic resonance, fluorescent capillary electrophoresis, lateral flow devices, colorimetry, chemiluminescence, fluorescence, western blots, microarrays, enzyme linked immunosorbent assay (ELISA), radioHPLC, single photon emission computed tomography (SPECT), or positron emission tomography (PET), radioimmunoassay (RIA), immunoradiometric assay, fluoroimmunoassay, chemiluminescent assay, and bioluminescent assay, though several others are well known to those of ordinary skill. The steps of various useful immunodetection methods have been described in the scientific literature.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

Further methods include the detection of primary immune complexes by a two-step approach. A second binding ligand, such as an antibody, that has binding affinity for the PDS/TTR is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed binding ligand. In this method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors. The present invention detects the presence of a PDS/TTR complex. This sequence can readily be modified to facilitate diagnostic assays, for example a tag (such as GFP) can be added to the targeting antibody to increase sensitivity. In one exemplary ELISA, antibodies are immobilized onto a selected surface exhibiting protein affinity, such as a well in a polystyrene microtiter plate. Then, a test composition suspected of containing the PDS/TTR complex, such as a clinical sample (e.g., a biological sample obtained from the subject), is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents. After binding and/or washing to remove non-specifically bound immune complexes, the bound anti-binding agents are detected. Where the initial binding agents are linked to a detectable label, the immune complexes may be detected directly. Again, the immune complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with anti-PDS or anti-TTP antibodies, one will generally incubate the wells of the plate with a solution of the antigen or antibodies, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the PDS/TTR complex with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

ASPECTS OF THE INVENTION

Accordingly, the invention can be seen, inter alia, in the following Aspects:

Aspect 1. A method of detecting a concentration of a biomarker in a human subject having or being at risk of developing Alzheimer's disease or Mild Cognitive Impairment (MCI), the method comprising: (a) detecting a first concentration of lipocalin-PDS/TTR complex in a blood sample or urine sample from the subject, (b) determining a second concentration of PDS/TTR complex in a blood sample or urine sample from an unaffected individual, and (c) comparing the first and second concentrations, wherein a lower first concentration as compared to the second concentration is indicative of the subject having or being at risk of developing Alzheimer's disease.

Aspect 2. A method of detecting a concentration of a biomarker in a human subject having or being at risk of developing Alzheimer's disease or Mild Cognitive Impairment (MCI), the method comprising: (a) detecting a concentration of lipocalin-PDS/TTR complex in a blood sample or urine sample from the subject, (b) comparing the concentration to a reference value, wherein a lower concentration as compared to the reference value is indicative of the subject having or being at risk of developing Alzheimer's disease or MCI.

Aspect 3. The method of Aspect 1 or Aspect 2, wherein the blood sample is a sample of whole blood, serum, plasma, or a subcomponent of blood.

Aspect 4. The method of any one of Aspects 1 to 3, wherein the blood sample is a serum or plasma sample.

Aspect 5. The method of any one of Aspects 1 to 4, wherein the lipocalin-PDS/TTR complex is a trimer consisting of one molecule of lipocalin-PDS and two molecules of TTR.

Aspect 6. The method of any one of Aspects 1 to 5, wherein the lipocalin-PDS/TTR complex binds to a trapping binding ligand specific for lipocalin-PDS but not to a binding ligand specific for hematopoietic-PDS/TTR complex.

Aspect 7. The method of Aspect 6, wherein the binding ligand is an antibody.

Aspect 8. The method of any one of Aspects 1 to 7, wherein the lipocalin-PDS/TTR complex is a modified lipocalin-PDS/TTR complex that further comprises alpha and/or beta-unsaturated aldehydic by-products of lipid peroxidation.

Aspect 9. The method of any one of Aspects 1 to 8, wherein the lipocalin-PDS/TTR complex binds to a probing binding ligand specific for TTR.

Aspect 10. The method of Aspect 9, wherein the probing ligand specific for TTR further comprises a label generating a detectable signal.

Aspect 11. The method of Aspect 10, wherein the label comprises a chemical, an enzymatic, a radioactive, a fluorescent, a luminescent, a chemiluminescent and a FRET label.

Aspect 12. The method of any one of Aspects 1 to 11, wherein the detection of the first concentration of lipocalin-PDS/TTR complex is by ELISA.

Aspect 13. A kit comprising (a) a solid substrate; (b) a trapping binding ligand specific for lipocalin-PDS bound to the solid substrate; (c) a probing binding ligand specific for TTR; (d) optionally, instructions for using the kit to detect PDS/TTR in a blood sample or urine sample.

Aspect 14. The kit of Aspect 13, wherein the solid substrate is a hydrocarbon polymer, glass, metal, or gel.

Aspect 15. The kit of Aspect 13, wherein the solid substrate is a gelatin, latex, polystyrene, colloidal gold or a magnetic bead.

Aspect 16. The kit of any one of Aspects 13 to 15, wherein trapping binding ligand specific for lipocalin-PDS but not to a binding ligand specific for hematopoietic-PDS.

Aspect 17. A method of isolating a lipocalin-PDS/TTR complex biomarker from blood or urine comprising: (a) contacting the blood or urine with a trapping binding ligand specific for lipocalin-PDS to form a trapped biomarker, wherein the trapping binding ligand specific for lipocalin-PDS is bound to a solid substrate; (b) contacting the trapped biomarker with a probing binding ligand that is specific for TTR to form a probed biomarker complex; and (c) purifying the probed biomarker complex.

Aspect 18. A probed biomarker complex isolated according to the method of Aspect 17.

Aspect 19. A process for detecting Alzheimer's disease (AD) or Mild Cognitive Impairment (MCI) in a human subject, the process comprising obtaining a sample of blood from the subject, preparing a sample of serum from the sample of blood, determining the concentration of PDS/TTR in the sample of serum, and comparing the concentration of PDS/TTR to a reference value.

Aspect 20. The process of Aspect 19, wherein AD or MCI is detected if the concentration of PDS/TTR is less than the reference value.

Aspect 21. The process of Aspect 19 or 20, wherein the sample of blood is collected from the subject by phlebotomy.

Aspect 22. The process of any one of Aspects 19 to 21, wherein the sample of serum is prepared from the sample of blood by permitting the sample of blood to clot and centrifuging the sample of blood.

Aspect 23. The process of any one of Aspects 19 to 22, wherein the concentration of PDS/TTR in the sample of serum is determined by ELISA.

Aspect 24. The process of any one of Aspects 19 to 23, wherein the ELISA is an ELISA described in U.S. Pat. No. 7,851,172.

Aspect 25. The process of any one of Aspects 19 to 24, wherein the ELISA provides an electromagnetic signal capable of being detected by an optical reader.

Aspect 26. The process of any one of Aspects 19 to 25, wherein the ELISA provides an electrochemical signal capable of being detected by an electrochemical signal detection apparatus.

The invention now will be described more fully hereinafter. In particular, aspects of the invention are more fully illustrated by the following examples, set forth to illustrate certain aspects of the present invention and not to be construed as limiting thereof. The invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

Example 1

The following experiments were carried out to verify that serum concentrations of a protein/protein complex formed through aldehydic crosslinking of one molecule of brain-specific (lipocalin) PDS and one dimer of TTR delineate between normal control (NC) subjects and patients with mild cognitive impairment (MCI) and/or probable Alzheimer's disease (AD). To determine if the PDS/TTR complex was present in serum of AD and NC subjects the inventors carried out immunoprecipitation studies of serum samples from three representative normal control (NC) subjects and 3 representative probable AD patients using rabbit anti-TTR as the trap antibody and mouse anti-lipocalin PDS as the probe antibody.

FIG. 1 shows the presence of a band at ~55 kDa corresponding to 1 molecule of PDS (23 kDa) crosslinked with 1 dimer (32 kDa) of TTR in serum samples and that levels are significantly ($p<0.05$) lower in probable AD patients (35.1±2.5% control) compared to NC subjects (100±2.9%). To further verify our hypothesis that levels of the PDS/TTR complex decrease in serum as they increase in CSF in MCI/AD, we used our previously described enzyme linked immunoassay (ELISA) developed for use with CSF specimens (with slight modification for serum analyses) to quantify levels of the PDS/TTR complex in postmortem ventricular CSF and antemortem serum from 11 autopsy-verified NC subjects and 5 MCI patients and found a strong negative correlation between CSF and serum levels of the complex for MCI patients ($r=-0.76$) but not for NC subjects ($r=0.28$). Based on these data, we used a PDS/TTR ELISA to analyze antemortem plasma specimens from 76 living NC subjects (43M/33W) and 45 MCI (26M/19W) patients. Subject demographic data are shown in Table 1. MCI subjects were significantly older and showed significantly lower MMSE scores compared to NC subjects. There was no difference in baseline MMSE scores of NC subjects who converted to MCI compared to those who remained controls. Table 1 shows there was a significant decrease in PDS/TTR concentrations in MCI subjects 356.5±11.9 ng/ml) compared to age-matched NC subjects (621.8±34.7 ng/ml) but no significant difference in $A\beta_{1-42}$ levels.

TABLE 1

Subject demographic data, PDS/TTR and Aβ1-42 concentrations.

| | Mean ± SEM Age (y) | Sex | Mean ± SEM MMSE | Mean ± SEM PDS/TTR Complex (ng/ml) | Mean ± SEM $A\beta_{1-42}$(pg/ml) |
|---|---|---|---|---|---|
| NC (N = 76) | 75.2 ± 0.8 | 43M/33W | 29.1 ± 0.1 | 621.8 ± 34.7 | 22.0 ± 2.2 |
| MCI (N = 45) | 79.9 0.9* | 26M/19W | 19.7 ± 1.6* | 356.5 ± 11.9* | 20.9 ± 2.8 |
| NC → NC (n = 37) | 72.9 ± 1.0 | 19M/18W | 29.2 ± 0.1 | 660.6 ± 36.7 | 23.1 ± 3.7 |
| NC → MCI (n = 29) | 77.9 ± 1.1* | 17M/12W | 28.6 ± 0.4 | 451.3 ± 42.1* | 23.1 ± 4.6 |

*p < 0.05

Figure 2:
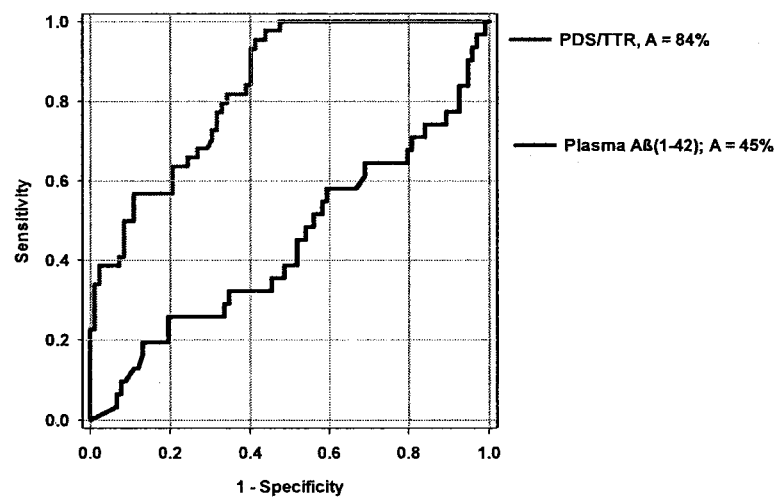
FIG. 2. Reporter operator curves for PDS/TTR and $A\beta_{1-42}$ in plasma from NC (N=76) and MCI (N=45) subjects. Improved sensitivity/specificity of the PDS/TTR complex is reflected by the increased area under the curve (AUC) for plasma PDS/TTR (AUC=84%) compared to an AUC of 45% for plasma $A\beta_{1-42}$ and 50% for CSF Aβ. Sensitivity/specificity of the PDS/TTR complex were 70% compared to sensitivity/specificity values of 52% and 44% respectively for Aβ measures.

Reporter operator curves (ROC) (FIG. 2) for comparison of the sensitivity/specificity for the identification of MCI patients from NC subjects for both PDS/TTR and $A\beta_{1-42}$ showed the PDS/TTR complex had an area under the curve (AUC) of 84% ($p<0.001$) with a sensitivity and specificity of 70% for the identification of MCI patients from NC subjects (cutoff=402.6 ng/ml). In contrast, $A\beta_{1-42}$ results showed an AUC of 44.6% with a sensitivity of 52% and a specificity of 44% for the same plasma samples.

Figures 3A, 3B:
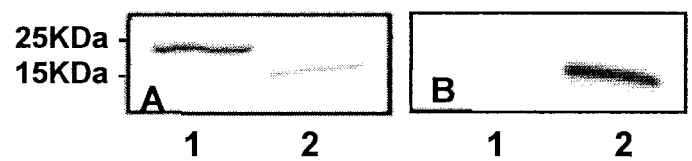
FIGS. 3A and 3B. Commossie blue stained gel (A) showing recombinant hematopoietic PDS (lane 1) and lipocalin PDS (lane 2) and the Western blot of a second gel probed using an anti-lipocalin PDS antibody (B).

The major difficulty in the development of a serum based bioassay for AD that relies on quantification of levels of brain specific proteins (lipocalin PDS) is the potential interference by blood associated proteins specifically hematopoietic (glutathione-dependent) PDS and additional TTR present in serum. To verify that our lipocalin-specific PDS antibody does not cross react with hematopoietic PDS, we subjected recombinant lipocalin and hematopoietic PDS to SDS-PAGE. FIG. 3A shows a Coomassie blue stained gel of hematopoietic PDS in Lane 1 and lipocalin PDS in Lane 2. FIG. 3B shows a Western blot of a separate gel stained using the anti-lipocalin PDS antibody. These figures demonstrate the lipocalin PDS antibody is specific for brain associated lipocalin PDS. To further verify that the presence of hematopoietic PDS or increased levels of TTR in serum do not interfere with quantification of lipocalin PDS using our ELISA we analyzed a representative serum sample alone or in the presence of recombinant hematopoietic PDS or TTR at concentrations between 15.75 ng/ml and 2000 ng/ml. Table 2 shows there were no significant differences in response of the ELISA in the presence of hematopoietic PDS or TTR even at 2000 ng/ml.

TABLE 2

Mean ± SEM ELISA response (% Control) for a representative serum sample probed without added hematopoietic PDS or TTR (Control) or in the presence of hematopoietic PDS or TTR at concentrations from 15.75 ng/ml to 2000 ng/ml. The presence of hematopoietic PDS or additional TTR did not significantly change the ELISA response at any concentration.

| | Concentration (ng/ml) | | | | | | | | |
|---|---|---|---|---|---|---|---|---|---|
| | 0 | 15.75 | 31.5 | 62.5 | 125 | 250 | 500 | 1000 | 2000 |
| Hematopoietic PDS | 100 ± 1.2% | 103.3 ± 2.6% | 100.7 ± 4.0% | 99.7 ± 4.2% | 100.7 ± 5.3% | 100.7 ± 8.6% | 107.8 ± 5.2% | 95.2 ± 18.8% | 93.9 ± 11.7% |
| TTR | 100 ± 1.2% | 119.1 ± 8.2% | 105.0 ± 3.6% | 101.7 ± 4.3% | 100.0 ± 6.7% | 110.4± 6.5% | 108.3 ± 3.5% | 109.8 ± 3.4% | 112.9 ± 5.4% |

Sample Processing: Blood samples were drawn from subjects. Blood samples were allowed to clot for 1 hour and centrifuged at 3,000×g for 5 minutes to separate serum. The serum was aliquoted into 1 ml single use aliquots and stored at −80° C. in the UK-ADC tissue repository until used for analysis.

ELISA Analyses: Quantification of PDS/TTR levels was carried out by generally following the inventors' ELISA that traps PDS and quantifies TTR complexed with the PDS described in U.S. Pat. No. 7,851,172, fully incorporated by reference herein. Samples were analyzed in triplicate and in a blind fashion. Because of the high protein content of serum samples SynBlock (Serotec) was used as a blocking agent and for dilution of trap and detection antibodies. Additionally, serum samples were diluted in 50 µl antigen capture buffer (5 mM NaH2PO4, 15 mM Na2PO4, 2 mM EDTA, 0.4 M NaCl, 0.5% CHAPS, 0.2% bovine serum albumin and 0.4% BSA block (Serotec) (pH 7.0) for analysis. All other parameters were as previously described. To allow comparison across plates, a representative quality control serum sample can be analyzed on all plates as an internal control specimen.

Example 2

Currently, clinical diagnosis of AD is based on physical and neurological examinations and neuropsychological examinations coupled with neuroimaging (structural and functional MRI, CT, PET and/or SPECT scans). Unfortunately, using current diagnostic criteria, AD is not definitively diagnosed until the disease has progressed to pronounced dementia (McKhann, G., et al., *Clinical diagnosis of Alzheimer's disease: report of the NINCDS-ADRDA Work Group under the auspices of Department of Health and Human Services Task Force on Alzheimer's Disease*. Neurology, 1984. 34(7): p. 939-44). In addition, current clinical diagnostic methods are not foolproof with accuracies between 65% and 90% (reviewed in Andreasen, N. and K. Blennow, *CSF biomarkers for mild cognitive impairment and early Alzheimer's disease*. Clin Neurol Neurosurg, 2005. 107(3): p. 165-73; Davidsson, P. and M. Sjogren, *Proteome studies of CSF in AD patients*. Mech Ageing Dev, 2006. 127(2): p. 133-7; de Leon, M. J., et al., *Longitudinal CSF and MRI biomarkers improve the diagnosis of mild cognitive impairment*. Neurobiol Aging, 2006. 27(3): p. 394-401; Maccioni, R. B., et al., *Biological markers of Alzheimer's disease and mild cognitive impairment*. Curr Alzheimer Res, 2004. 1(4): p. 307-14) with higher rates associated with specialized memory disorder clinics, whereas lower rates are associated with primary care clinics. Also, the accuracy of clinical diagnosis of AD is likely lower during prodromal stages of the disease or for older, or poorly educated subjects (reviewed in (de Leon, M. J., et al., *Longitudinal CSF and MRI biomarkers improve the diagnosis of mild cognitive impairment*. Neurobiol Aging, 2006. 27(3): p. 394-401). With increasing availability of potentially beneficial therapeutics, patients are seeking medical intervention at earlier stages of the disease. Previous studies suggest preclinical stages of AD may begin 20 to 30 years before onset of clinical symptoms (reviewed Blennow, K., *Cerebrospinal fluid protein biomarkers for Alzheimer's disease*. NeuroRx, 2004. 1(2): p. 213-25) and that during this prodromal phase, neuronal degeneration and senile plaque (SP) formation increase until a threshold is reached where episodic memory impairment occurs, a transition between normal aging and dementia described as amnestic mild cognitive impairment (MCI).

Difficulties associated with diagnosis of AD has generated considerable interest in the identification of a reliable protein based biomarkers of AD that could aid clinicians in more readily diagnosing AD at earlier stages before symptoms of dementia appear (Davidsson, P. and M. Sjogren, *Proteome studies of CSF in AD patients*. Mech Ageing Dev, 2006. 127(2): p. 133-7). Ideally, these biomarkers are characteristic molecules, typically proteins or protein fragments, that are based on some fundamental feature of AD neuropathology and can be objectively measured and evaluated in a reasonably sampled body fluid as an indicator of a pathogenic process or the response to therapeutic interventions (reviewed in Andreasen, N. and K. Blennow, *CSF biomarkers for mild cognitive impairment and early Alzheimer's disease*. Clin Neurol Neurosurg, 2005. 107(3): p. 165-73; de Leon, M. J., et al., *Longitudinal CSF and MRI biomarkers improve the diagnosis of mild cognitive impairment*. Neurobiol Aging, 2006. 27(3): p. 394-401; Maccioni, R. B., et al., *Biological markers of Alzheimer's disease and mild cognitive impairment*. Curr Alzheimer Res, 2004. 1(4): p. 307-14).

Current Biomarkers of AD in Blood

Although multiple potential biomarkers of AD have been identified and studied in CSF, lumbar puncture is not a widespread practice in primary care or geriatric clinics and is not routinely carried out during evaluation of AD patients. Therefore, biomarkers of AD in blood (serum or plasma) that would allow more widely applicable, minimally invasive and less expensive testing of patients are critically needed. The primary difficulty in the development of a serum based AD diagnostic is the physiology of the blood-brain and blood-CSF barriers that typically limits the transfer of potentially diagnostic molecules to the blood. Additionally, dilution of brain specific proteins or protein fragments in blood make detection more difficult. Currently, the most widely studied potential biomarkers of AD in blood include those related to Aβ processing (Aβ$_{1-42}$, Aβ$_{1-40}$ and the ratio of Aβ$_{1-42}$/Aβ$_{1-40}$) and inflammation.

Aβ as a Biomarker

As observed for CSF, diminished levels of Aβ$_{1-42}$ in blood are thought to reflect deposition in SP in the brain. Comparison of blood and CSF levels of Aβ shows a 100-fold decrease in plasma compared to CSF (reviewed in Solfrizzi, V., et al., *Circulating biomarkers of cognitive decline and dementia*. Clin Chim Acta, 2006. 364(1-2): p. 91-112). Studies of the relationship between plasma Aβ and cognitive impairment have been contradictory. Multiple cross sectional and longitudinal studies have shown evaluated plasma Aβ levels in MCI and AD whereas most show no differences between AD and NC subjects for Aβ$_{1-40}$ levels. Studies of Aβ$_{1-42}$ show similar results for AD and NC subjects although more recent longitudinal data suggest high plasma Aβ$_{1-42}$ levels were a risk factor for the development of AD. Case control studies of MCI and NC subjects showed lower Aβ$_{1-42}$ levels in MCI patients, although they did not correlate with disease progression or with severity of dementia. More recent studies show no significant differences in multiple Aβ species between AD and control groups although lower Aβ$_{1-42}$/Aβ$_{N-42}$ ratios were observed for demented (AD and non-AD) subjects compared to normal controls (Le Bastard, N., et al., *Plasma amyloid-beta forms in Alzheimer's disease and non Alzheimer's disease patients*. Journal of Alzheimer's disease: JAD, 2010. 21(1): p. 291-301). Another study suggested high baseline plasma Aβ$_{42}$ and Aβ$_{40}$ with decreasing Aβ$_{42}$ levels on follow-up were associated with more pronounced decline in multiple cognitive domains (Cosentino, S. A., et al., *Plasma ss-amyloid and cognitive decline*. Archives of neurology, 2010. 67(12): p. 1485-90).

Despite the initial promise associated with plasma Aβ as a biomarker of AD, current data suggest plasma Aβ levels alone do not demonstrate sufficient sensitivity or specificity as a diagnostic biomarker of AD. More recently, studies have focused on quantification of levels of APP in platelets which is cleaved following platelet activation to yield carboxy-truncated fragments of 110 or 120 to 130 kDa and suggest a decrease in the 130 kDa/110 kDa ratio is present in MCI and AD patients but not in NC or patients with other neurological disorders. The APP isoform ratio correlated with disease progression and severity and demonstrated diagnostic sensitivities/specificities of 80-90% although the relationship between levels of platelet specific APP and brain alterations remains unclear.

Inflammatory Cytokines as Biomarkers of AD

Multiple studies show abnormal levels of various inflammatory cytokines in brain regions affected in AD. However, it remains unclear if accumulation of inflammatory molecules in brain would be reflected accurately in serum/plasma. Studies of IL-6 in blood have been contradictory with reports of elevations in AD or no changes. Similar results have been observed for several other cytokines including TNF-α and TGF-β. In more recent studies (Ray et al., *Classification and prediction of clinical Alzheimer's diagnosis based on plasma signaling proteins*. Nat Med, 2007. 13(11): p. 1359-62) using a multiplex analysis identified multiple signaling proteins in plasma including G-CSF, IL-1α, IL-3, IL-11, GM-CSF, PDGF-BB and TNFα that in combination, differentiated patients with AD from age-matched NC subjects.

There is considerable need for the identification and validation of alternative molecules that alone or in combination with others would allow non-invasive tests for early detection of AD. Based on our study demonstrating increased levels of an aberrant protein/protein complex consisting of 1 molecule of brain-specific (lipocalin) prostaglandin-d-synthase (PDS; Swiss-Prot#P41222) and 1 dimer of transthyretin (TTR; Swiss-Prot#P02766) in CSF that delineated AD from NC and DC subjects (Lovell, M. A., et al., *An aberrant protein complex in CSF as a biomarker of Alzheimer disease*. Neurology, 2008. 70(23): p. 2212-8) coupled with preliminary unpublished data suggesting that cultured choroid plexus epithelial cells established from AD and MCI subjects lose their capacity to transport large molecules from brain compared to cultures from NC subjects, we hypothesized that levels of the PDS/TTR complex would decrease in blood during disease progression and would likely reflect diminished choroid plexus function. Although glycosylation, phosphorylation, acetylation and oxidative modifications have been identified for specific isoforms of PDS in AD, PD, and ALS CSF (reviewed in Harrington, M. G., et al., *Prostaglandin D synthase isoforms from cerebrospinal fluid vary with brain pathology*. Dis Markers, 2006. 22(1-2): p. 73-81) the association of PDS with classical pathogenic cascades remains unclear. Similarly, TTR which is functionally active as a homotetramer composed of 4 monomers (MW=16 kDa) arranged as a dimer of dimers is of potential interest in AD because mutations of the TTR gene are the most common cause of autosomal dominant systemic amyloidoses underlying familial amyloid polyneuropathy (FAP) that is characterized by high abundance TTR present in β-structured fibrils. Diminished native TTR is suggested to negatively affect Aβ aggregation and alter thyroxine transport leading to neurodegeneration (Serot, J. M., et al., *Cerebrospinal fluid transthyretin: aging and late onset Alzheimer's disease*. J Neurol Neurosurg Psychiatry, 1997. 63(4): p. 506-8). Although no mutations of TTR have been identified in AD, TTR overexpression is neuroprotective in AD animal models (Stein, T. D., et al., *Neutralization of transthyretin reverses the neuroprotective effects of secreted amyloid precursor protein (APP) in APPSW mice resulting in tau phosphorylation and loss of hippocampal neurons: support for the amyloid hypothesis*. J Neurosci, 2004. 24(35): p. 7707-17).

Considerable research effort has been directed at the study of levels of Aβ$_{1-42}$ and Aβ$_{1-40}$ or ratios of the two as potential diagnostic biomarkers of AD. Unfortunately, the studies are been somewhat contradictory leaving a need for evaluation of additional novel serum/plasma biomarkers of the disease. The aims described in this proposal are innovative in that they are directed at the potential diagnostic efficacy of a novel biomarker of disease that appears to have improved sensitivity/specificity compared to measures of Aβ. In addition, the proposed studies will evaluate potential synergies between our novel biomarker and more established markers to evaluate potential enhancement of diagnostic efficacy of the individual measures.

Immunoprecipitation studies of serum samples from 3 representative NC subjects and 3 probable AD patients using mouse anti-PDS as the trap antibody and rabbit anti-TTR as the probe antibody, identified a band at ~55 kDa corresponding to 1 molecule of PDS (23 kDa) crosslinked with 1 dimer (32 kDa) of TTR in serum. Levels of the complex were significantly ($p<0.05$) lower in probable AD patients (35.1±2.5% control) compared to NC subjects (100±2.9%). To further verify our hypothesis that levels of the PDS/TTR complex decrease in serum as they increase in CSF in MCI/AD, we used our previously described enzyme linked immunoassay (ELISA) developed for use with CSF specimens (Lovell, M. A., et al., *An aberrant protein complex in CSF as a biomarker of Alzheimer disease.* Neurology, 2008. 70(23): p. 2212-8) (with slight modification for serum analyses) to quantify levels of the PDS/TTR complex in postmortem ventricular CSF and antemortem serum from 11 autopsy-verified NC subjects and 5 MCI patients and found a strong negative correlation between CSF and serum levels of the complex for MCI patients ($r=-0.76$) but not for NC subjects ($r=0.28$). To allow comparison of results of our PDS/TTR measures with the more established marker Aβ, we tested paired serum/plasma samples from probable AD and NC subjects and found that plasma concentrations of the complex were higher than those observed in serum. Based on these data we used our PDS/TTR ELISA to analyze antemortem plasma specimens from 76 living NC subjects (43M/33W) and 45 MCI (26M/19W) patients. Subject demographic data are shown in Table 3. MCI subjects were significantly older and showed significantly lower MMSE scores compared to NC subjects. There was no difference in baseline MMSE scores of NC subjects who converted to MCI compared to those who remained controls. Table 3 shows there was a significant decrease in PDS/TTR concentrations in MCI subjects 356.5±11.9 ng/ml) compared to age-matched NC subjects (621.8±34.7 ng/ml) but no significant difference in $A\beta_{1-42}$ levels.

with immunizing peptides showed the lipocalin PDS antibody is specific for brain associated lipocalin PDS (data not shown). Analysis of a representative plasma sample alone or with recombinant hematopoietic PDS or TTR added at concentrations between 15.75 ng/ml and 2000 ng/ml showed no significant difference in response of the ELISA.

Example 3

To test if serum PDS/TTR complex concentrations decrease in the same person following conversion to MCI by analyzing pre- and post-conversion serum specimens from NC subjects who transitioned from normal to MCI or AD compared to results obtained for serum samples from control subjects who remained cognitively normal after a comparable follow-up period. We analyzed plasma samples obtained from 28 MCI patients before and after conversion from NC status to MCI and showed a significant 31.6±8.5% decrease in levels of PDS/TTR for MCI patients following conversion compared to 43 NC subjects who remained cognitively normal after a comparable follow-up period. Table 4 shows mean±SEM percent change in PDS/TTR concentrations, MMSE scores and Aβ levels and shows a significantly more pronounced change in PDS/TTR concentrations in MCI patients compared to changes in MMSE or Aβ levels suggesting levels of the complex may be a more sensitive indicator of disease progression. In addition, based on PDS/TTR concentrations measured in initial plasma draws we identified a subset of 10 NC subjects with unusually low PDS/TTR concentrations who remained cognitively normal at the second plasma draw but who showed significantly diminished scores on logical memory tasks at subsequent draws.

TABLE 3

Subject demographic data, PDS/TTR and Aβ1-42 concentrations.

| | Mean ± SEM Age (y) | Sex | Mean ± SEM MMSE | Mean ± SEM PDS/TTR Complex (ng/ml) | Mean ± SEM $A\beta_{1-42}$ (pg/ml) |
|---|---|---|---|---|---|
| NC (N = 76) | 75.2 ± 0.8 | 43M/33W | 29.1 ± 0.1 | 621.8 ± 34.7 | 22.0 ± 2.2 |
| MCI (N = 45) | 79.9 0.9* | 26M/19W | 19.7 ± 1.6* | 356.5 ± 11.9* | 20.9 ± 2.8 |
| NC → NC (n = 37) | 72.9 ± 1.0 | 19M/18W | 29.2 ± 0.1 | 660.6 ± 36.7 | 23.1 ± 3.7 |
| NC → MCI (n = 29) | 77.9 ± 1.1* | 17M/12W | 28.6 ± 0.4 | 451.3 ± 42.1* | 23.1 ± 4.6 |

*p < 0.05

Reporter operator curves (ROC) (FIG. 2) for comparison of the sensitivity/specificity for the identification of MCI patients from NC subjects for both PDS/TTR and $A\beta_{1-42}$ showed the PDS/TTR complex had an area under the curve (AUC) of 84% ($p<0.001$) with a sensitivity and specificity of 70% for the identification of MCI patients from NC subjects (cutoff=402.6 ng/ml). In contrast, $A\beta_{1-42}$ results showed an AUC of 44.6% with a sensitivity of 52% and a specificity of 44% for the same plasma samples.

Potential interference by blood associated proteins, specifically hematopoietic (glutathione-dependent) PDS and additional TTR present in blood are potential analytical difficulties. Western blot analysis using antibodies blocked

TABLE 4

| | Mean ± SEM % Change PDS/TTR | Mean ± SEM % Change in $A\beta_{1-42}$ | Mean ± SEM % Change in MMSE |
|---|---|---|---|
| NC → NC | 9.0 ± 5.3 | 3.1 ± 1.3 | -1.2 ± 0.01 |
| NC → MCI | -22.3 ± 2.9* | 23.3 ± 13.4 | -6.3 ± 1.5* |

Mean ± SEM % change in PDS/TTR concentration is significantly larger than changes in MMSE or Aβ1-42 levels.
*p < 0.05.

Overall, the data suggest that quantification of levels of the PDS/TTR complex in plasma may be effective in the identification of AD subjects including those early in disease progression (MCI patients). Early identification of AD would allow pharmacologic interventions that could delay cognitive decline associated with AD and improve the quality of life for those subjects. The proposed test could also be used as a screen to better identify subjects for inclusion in clinical trials of potential therapeutics thereby minimizing the number of subjects needed to insure a sufficient number of subjects convert to AD during the trial. In our preliminary studies, the PDS/TTR complex was reliable, reproducible, and provided the necessary sensitivity/specificity for the identification of subjects early in disease progression (MCI).

Every reference cited herein is incorporated fully by reference. To the extent that there is any conflict between the teaching of any reference and that of the instant specification, the teaching of the instant specification shall control.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of detecting lipocalin-prostaglandin-d-synthase/transthyretin (PDS/TTR) biomarker complex in a human subject suspected of having Alzheimer's disease or mild cognitive impairment, comprising:
   (i) obtaining a blood sample or urine sample from the human subject suspected of having Alzheimer's disease or mild cognitive impairment; and
   (ii) detecting the lipocalin-prostaglandin-d-synthase/transthyretin (PDS/TTR) complex in the blood sample or urine sample from the subject by contacting the sample with a trapping binding ligand that is an anti-lipocalin-PDS antibody followed by contacting the sample from the subject with a probing binding ligand that is an anti-TTR antibody to obtain a lipocalin-PDS/TTR complex.

2. The method of claim 1, wherein the anti-lipocalin PDS antibody is a mouse anti-lipocalin-PDS antibody, and the anti-TTR antibody is a rabbit anti-TTR antibody.

3. The method of claim 1, wherein the blood sample is a sample of whole blood, serum, plasma, or a subcomponent of blood.

4. The method of claim 1, wherein the blood sample is a serum or plasma sample.

5. The method of claim 1, wherein the probing binding ligand specific for TTR further comprises a label generating a detectable signal.

6. The method of claim 5, wherein the label comprises a chemical, an enzymatic, a radioactive, a fluorescent, a luminescent, a chemiluminescent or a Fluorescence Resonance Energy Transfer (FRET) label.

7. The method of claim 1, wherein the detection of the lipocalin-PDS/TTR complex is by enzyme-linked immunosorbent assay (ELISA).

8. The method of claim 1, wherein the detection of the lipocalin-PDS/TTR complex is by enzyme-linked immunosorbent assay (ELISA), and wherein the lipocalin-PDS/TTR biomarker complex is a trimer consisting of one molecule of lipocalin-PDS and two molecules of TTR.

9. The method of claim 2, wherein the rabbit anti-TTR antibody further comprises a label generating a detectable signal.

10. The method of claim 9, wherein the label comprises a chemical, an enzymatic, a radioactive, a fluorescent, a luminescent, a chemiluminescent or a Fluorescence Resonance Energy Transfer (FRET) label.

11. The method of claim 1, and further comprising determining whether there is a lower concentration of lipocalin-PDS/TTR complex in the sample than in a normal control.

* * * * *